US006245298B1

United States Patent
Bremer et al.

(10) Patent No.: US 6,245,298 B1
(45) Date of Patent: Jun. 12, 2001

(54) SAMPLE APPLICATION DEVICE FOR A GAS CHROMATOGRAPH

(75) Inventors: Ralf Bremer, Oberhausen; Bernhard Rose, Dusseldorf, both of (DE)

(73) Assignee: Gerstel GmbH & Co., KG, Mulheim (DE)

( * ) Notice: Subject to any disclaimer, the term of this patent is extended or adjusted under 35 U.S.C. 154(b) by 0 days.

(21) Appl. No.: 09/293,668

(22) Filed: Apr. 16, 1999

(30) Foreign Application Priority Data

Apr. 17, 1998 (DE) .............................................. 198 17 016

(51) Int. Cl.[7] .................................................. G01N 30/04
(52) U.S. Cl. ........................... 422/80; 422/68.1; 422/307; 436/155
(58) Field of Search ...................... 422/78, 103

(56) References Cited

U.S. PATENT DOCUMENTS

| 4,087,249 | * | 5/1978 | Okumoto et al. | 23/253 PC |
|---|---|---|---|---|
| 4,294,117 | * | 10/1981 | Buser | 73/864.85 |
| 4,344,917 | * | 8/1982 | Schorno | 422/78 |
| 4,559,063 | * | 12/1985 | Munari et al. | 55/67 |
| 4,919,893 | * | 4/1990 | Bandurski et al. | 422/78 |
| 5,009,591 | * | 4/1991 | Watanabe | 432/128 |
| 5,544,276 | * | 8/1996 | Loux et al. | 392/480 |
| 5,654,636 | * | 8/1997 | Sweedler et al. | 324/321 |
| 5,702,671 | * | 12/1997 | Gerstel | 422/103 |
| 6,055,845 | * | 5/2000 | Gerstel et al. | 73/23.42 |

FOREIGN PATENT DOCUMENTS

9853310 * 11/1998 (WO) .

* cited by examiner

*Primary Examiner*—Jill Warden
*Assistant Examiner*—Yelena Gakh
(74) *Attorney, Agent, or Firm*—Townsend and Townsend and Crew LLP

(57) ABSTRACT

The invention relates to a sample application device for a gas chromatograph, having an evaporator (1) which can be cooled, can be heated in a temperature-controlled manner, is provided with a carrier-gas feed and has a valve head (11) for holding an exchangeable sampling tube (27), a receiving chamber (4) for the sampling tube (27), a column exit (18) and, if appropriate, a splitter exit (31). In this device, a pyrolyser tube (20), which is coupled to the carrier-gas feed and is held by the valve head (11), is arranged in the receiving chamber (4), in which there is a heating coil (26) into which the sampling tube (27) can be fitted and to which current can be applied by means of a heating conductor (25) which is guided outwards through the valve head (11).

9 Claims, 2 Drawing Sheets

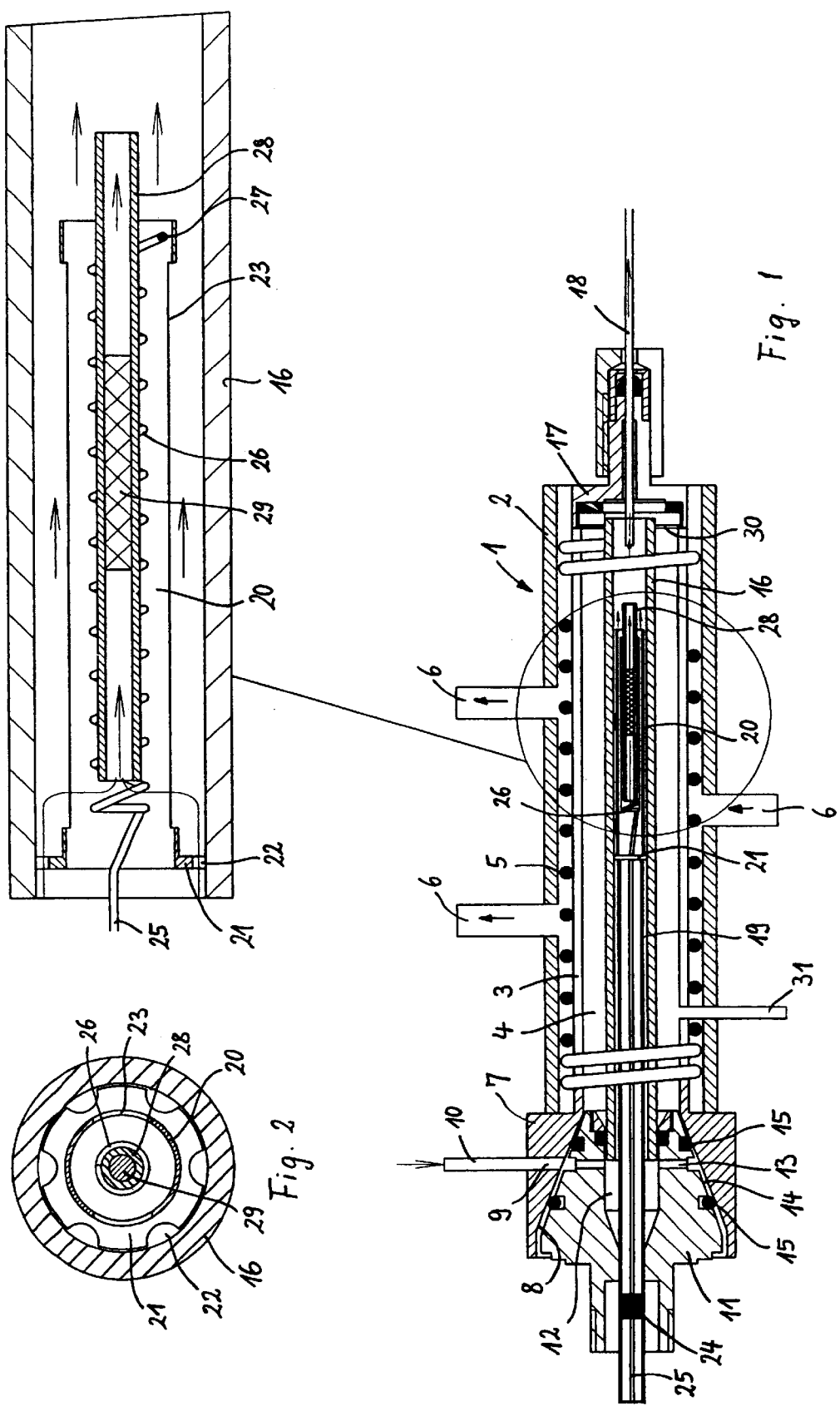

SAMPLE APPLICATION DEVICE FOR A GAS CHROMATOGRAPH

FIELD OF THE INVENTION

The invention relates to a sample application device for a gas chromatograph.

DESCRIPTION OF THE RELATED ART

German Patent DE 196 53 406 C1 discloses a sample application device for a gas chromatograph, having an evaporator which can be cooled, can be heated in a temperature-controlled manner, is provided with a carrier-gas feed and has a valve head for holding an exchangeable sampling tube, a receiving chamber for the sampling tube, a column exit and, if appropriate, a splitter exit. This device is used to transfer substances which have been liberated from the sample material by thermodesorption to a capillary column (transfer column or separation column of a gas chromatograph) by means of carrier gas. A sample application device of this nature makes it possible to carry out decomposition-free gas-phase extraction with regard to solid samples, for example at ambient or, if appropriate, at elevated operating temperatures.

Furthermore, it is known to subject sample material to pyrolysis, with the products formed as a result of this pyrolysis being analyzed by gas chromatography. The pyrolysis takes place at substantially higher temperatures than decomposition-free gas-phase extraction, and is not decomposition-free; rather, the aim is to analyse decomposition or reaction products formed at high temperatures. However, it is not possible in this process to distinguish between substances which are released without decomposition at relatively low temperatures and those which are only formed during the pyrolysis.

SUMMARY OF THE INVENTION

It is an object of the invention is to provide a sample application device for a gas chromatograph which makes it possible to analyse the complete gas-phase stripping products of a sample by gas chromatography. It is a further object of the invention to provide a sample application device which permits the analysis of the stripping products of a sample obtained at suitably low temperatures through to products from this sample formed by thermal decomposition during the pyrolysis. It is still a further object of the invention to provide a sample application which permits the analysis of the stripping products of a sample obtained at suitably low temperatures through to products from this sample formed by thermal decomposition during the pyrolysis within one step.

A subject of the invention is a sample application device for a gas chromatograph, comprising:

- an evaporator provided with a cooling device for cooling the evaporator and a heating device for heating the evaporator in a temperature-controlled manner, and further provided with a carrier-gas feed, a valve head for holding an exchangeable sampling tube, a receiving chamber for the sampling tube, and a column exit; and
- a pyrolyzer tube coupled to the carrier-gas feed and held by the valve head,
- wherein the pyrolyzer tube is arranged in the receiving chamber, and
- wherein a heating coil is provided in the receiving chamber, into said heating coil the sampling tube is insertable and to which current is applicable by means of a heating conductor which is guided outwards through the valve head.

By using such a device, it is possible to analyze samples by gas chromatography both with regard to the substances formed during decomposition-free gas-phase stripping at suitably low temperatures and with regard to the products formed by thermal decomposition during pyrolysis, it being possible for this analysis to be carried out in a single arrangement in one step, in succession, on the same sample, so that it is possible to differentiate between the substances formed during decomposition-free gas-phase stripping and the pyrolysis decomposition products in the chromatogram. Moreover, it becomes possible to apply substances formed by decomposition-free gas-phase extraction and products formed by pyrolysis independently of one another.

Further objects, advantages and embodiments of the invention are evident from the following description.

The invention is explained in more detail below with reference to an exemplary embodiment illustrated in the appended drawings.

BRIEF DESCRIPTION OF THE DRAWINGS

FIG. 1 shows a diagrammatic, partially sectional view of a sample application device for a gas chromatograph according to the invention which has a temperature-controlled oven, which is provided with a carrier-gas connection and is not shown, as well as an enlarged detail of this gas chromatograph.

FIG. 2 shows a section on line II—II from FIG. 1.

DETAILED DESCRIPTION OF A PREFERRED EMBODIMENT

Figure 3:
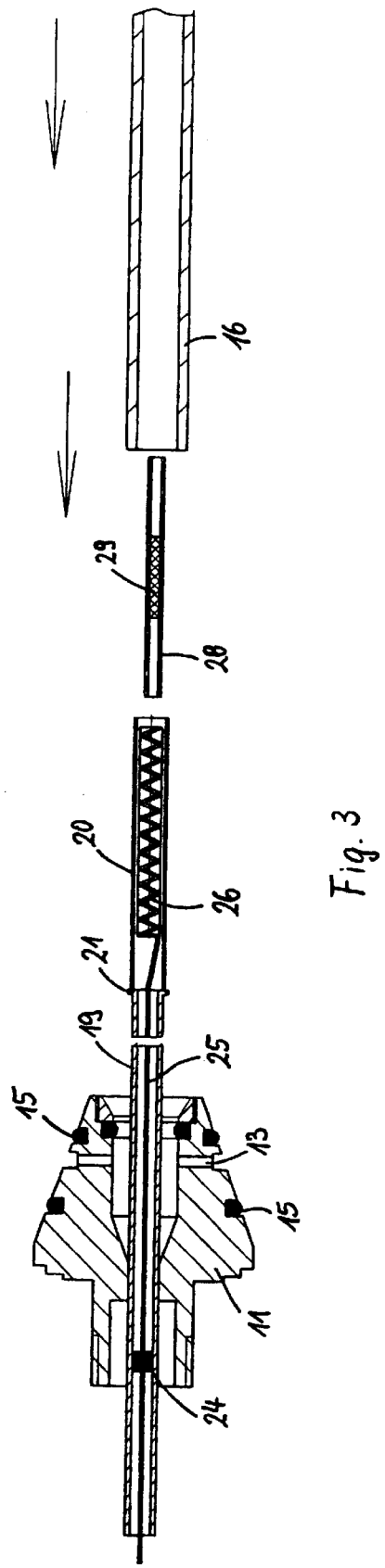
FIG. 3 shows an exploded view of part of the sample application device from FIG. 1.

The thermodesorption device of the invention illustrated comprises an evaporator 1 which can be cooled, can be heated in a controlled manner and has a cylindrical outer casing 2 and a cylindrical inner casing 3 arranged concentrically with respect to the outer casing, this inner casing delimiting an inner receiving chamber 4. A heating coil 5 of a heating device for the controlled heating of the receiving chamber 4 is arranged between outer casing 2 and inner casing 3, both of which are made from metal, while, furthermore, coolant bores 6 lead into the area between outer casing 2 and inner casing 3, in order to feed through a coolant, for example liquid nitrogen, and thus to cool the receiving chamber 4.

At one end, the inner casing 3 is connected, if appropriate as a single unit, to a receiving piece 7 which has a frusto-conical recess 8 which opens into the receiving chamber 4. The receiving piece 7 has a radial bore 9 which opens into the recess 8 and is connected to a feed line 10 for carrier gas.

The recess 8 serves to accommodate a frustoconical valve body 11 which is provided with a stepped through-bore 12 which is coaxial with respect to the receiving chamber 4. Moreover, the valve body 11 has a transverse bore 13 which opens into an annular space 14 between two O-ring seals 15 between valve body 11 and receiving piece 7, into which annular space the radial bore 9 also opens. This ensures the carrier-gas feed to the through-bore 12.

A metal casing tube 16 is fitted in a sealed manner into the receiving-chamber-side end of the through-bore 12. The opposite end of the casing tube 16 is accommodated by a holder 17 which is sealed with respect to the outside and delimits the corresponding end of the receiver chamber 4. A capillary 18, for example a gas-chromatography separating capillary or transfer capillary, is fitted in a sealed manner through the holder 17, leaving an annular space with respect to the surrounding casing tube 16.

Furthermore, the casing tube 16 accommodates a guide tube 19 which extends outwards through the through-bore 12 in the valve body 11, and a pyrolyzer tube 20 is arranged, for example fitted onto, the casing-tube-side end, which pyrolyzer tube has a centering flange 21 which centers the pyrolyzer tube 20 and the guide tube 19 with respect to the surrounding casing tube 16. The centering flange 21 has passage openings 22 which are distributed over the circumference. The pyrolyzer tube 20 is provided with slots 23 which extend in its longitudinal direction.

A heating conductor 25, which is at a distance from or insulated from the guide tube 19, is guided through the guide tube 19, sealed off by means of a seal 24, which heating conductor, in the pyrolyzer tube 20, forms a heating coil 26 which is arranged at a distance from the pyrolyser tube and is soldered to the pyrolyser tube 20 at the location indicated by 27. As an alternative, the heating conductor 25 may also be a bifilar winding so as to form a heating coil 26.

A sampling tube 28, which is made, for example, from quartz or the like and contains a sample 29 which is to be analyzed, can be fitted into the heating coil 26.

To provide the sample application device with a sample 29, firstly the sampling tube 28 accommodating this sample is fitted into the heating coil 26, and then the casing tube 16 is pushed on until it is received by the through-bore 12 in the valve body 11, after which the valve body 11, together with the parts it supports, is inserted into the recess 8 in the receiving piece 7, and as a result the parts which the valve body supports are fitted into the receiving chamber 4.

The heating coil 26 can be used to carry out pyrolytic degassing of the sample 29 at a suitably high temperature. Gas or vapor products formed in this process can be removed by means of carrier gas, which flows out of the radial bore 13 into the space between casing tube 16 and guide tube 19 and, from there, through the openings 22 in the centering flange 21 and the slots 23, into the sampling tube 28, and past this tube and the pyrolyzer tube 20, in order to be fed either to the capillary 18 or, where the capillary 18 is (pneumatically) closed, to a splitter exit 31 from the receiving chamber 4 via openings 30 in the holder 17 and the receiving chamber 4. The splitter exit may also be arranged in the area of the holder 17 or downstream of this area.

The temperature used for the pyrolysis can be determined by periodically connecting the heating coil 26 for a short time to a measurement duct in which the temperature is determined, for example from the instantaneous resistance.

The sample application device can also be used without pyrolysis for thermodesorption, in which case the heating coil 26 can again be used to determine the temperature during the thermodesorption. Moreover, thermodesorption may be followed by pyrolysis.

The sample application tube 28 is in this case used as a disposable item, i.e. a new sample application tube 28 is used for each analysis.

What is claimed is:

1. In a sample application device for a gas chromatograph comprising:

an evaporator comprising (i) a receiving chamber having an inlet and exit, (ii) a valve head positioned at said inlet, (iii) an exchangeable sampling tube disposed within said receiving chamber and held therein by said valve head, (iv) cooling means and (v) temperature controlled heating means surrounding said sampling tube for cooling and heating, respectively, said sampling tube, (vi) means for supplying carrier gas and directing said carrier gas through said sampling tube, and (vii) means for connecting said exit to a chromatographic column, the improvement comprising:

a pyrolyzer tube within said temperature controlled heating means and surrounding said sampling tube and held within said receiving chamber by said valve head, said pyrolyzer tube communicating with said means for supplying carrier gas to pass carrier gas through said sampling tube toward said exit, and a heating coil disposed inside said pyrolyzer tube and sized to receive said sampling tube, said heating coil connectable to an external power source through a conductor passing through said valve head.

2. A sample application device in accordance with claim 1 further comprising a guide tube affixed to said pyrolyzer tube to receive said conductor.

3. A sample application device in accordance with claim 1 further comprising a casing tube disposed inside said evaporator, surrounding said pyrolyzer tube, and capable of being affixed to said valve head.

4. A sample application device in accordance with claim 3 further comprising means for centering said pyrolyzer tube in said casing tube.

5. A sample application device in accordance with claim 3 in which said means for supplying carrier gas and directing said carrier gas through said sampling tube comprise a gap between said pyrolyzer tube and said casing tube and a slot in said pyrolyzer tube to permit entry of said carrier gas into said sampling tube.

6. A sample application device in accordance with claim 3 further comprising a centering flange for centering said pyrolyzer tube in said casing tube, said centering flange containing openings for passage of said carrier gas.

7. A sample application device in accordance with claim 1 in which an end of said heating coil is soldered to said pyrolyzer tube.

8. A sample application device in accordance with claim 1 in which said heating coil is a bifilar winding.

9. A sample application device in accordance with claim 1 in which said evaporator is provided with a splitter exit.

* * * * *